(12) United States Patent
Feiweier et al.

(10) Patent No.: US 7,492,349 B2
(45) Date of Patent: Feb. 17, 2009

(54) MAGNETIC RESONANCE TOMOGRAPHY APPARATUS WITH STEP-FREE FADE BETWEEN DISPLAYED DIFFERENT SPIN ENSEMBLES

(75) Inventors: Thorsten Feiweier, Spardorf (DE); Peter Heubes, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 642 days.

(21) Appl. No.: 10/123,394

(22) Filed: Apr. 16, 2002

(65) Prior Publication Data

US 2002/0183614 A1 Dec. 5, 2002

(30) Foreign Application Priority Data

Apr. 23, 2001 (DE) ................................. 101 19 784

(51) Int. Cl.
*G09G 5/00* (2006.01)
(52) U.S. Cl. ....................... 345/156; 382/128; 324/307; 324/309; 345/418; 600/407
(58) Field of Classification Search ................ 600/407, 600/410, 431, 425, 443; 324/307, 309, 311; 345/419, 156, 418; 128/916; 382/128
See application file for complete search history.

(56) References Cited

U.S. PATENT DOCUMENTS

| | | | | |
|---|---|---|---|---|
| 4,949,042 A | * | 8/1990 | Kuhara et al. | 324/311 |
| 5,155,435 A | * | 10/1992 | Kaufman et al. | 324/309 |
| 5,187,439 A | * | 2/1993 | Jensen et al. | 324/309 |
| 5,454,371 A | * | 10/1995 | Fenster et al. | 600/443 |
| 5,594,849 A | | 1/1997 | Kue et al. | |
| 6,333,752 B1 | * | 12/2001 | Hasegawa et al. | 715/764 |
| 6,459,922 B1 | * | 10/2002 | Zhang | 600/410 |
| 6,512,530 B1 | * | 1/2003 | Rzepkowski et al. | 715/833 |
| 6,580,936 B2 | | 6/2003 | Muraki et al. | |
| 6,586,934 B2 | * | 7/2003 | Biglieri et al. | 324/309 |

OTHER PUBLICATIONS

Abstract of JP6189938, and partial translation thereof.

* cited by examiner

*Primary Examiner*—Brian L. Casler
*Assistant Examiner*—Baisakhi Roy
(74) *Attorney, Agent, or Firm*—Schiff Hardin LLP

(57) ABSTRACT

In an apparatus for processing and presenting a magnetic resonance tomography measured image wherein following simultaneous calculation of the contrast images of various spin ensembles or various MR images of a spin ensemble (anatomical, angiographic, functional), a step-free fade of the contrast images can be undertaken with an input device. A multi-colored presentation can be used in addition to the gray scale presentation dependent on the spin ensemble.

8 Claims, 3 Drawing Sheets

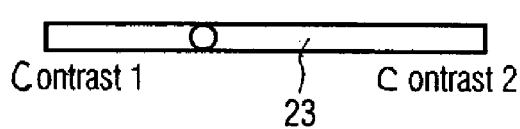
FIG 2a
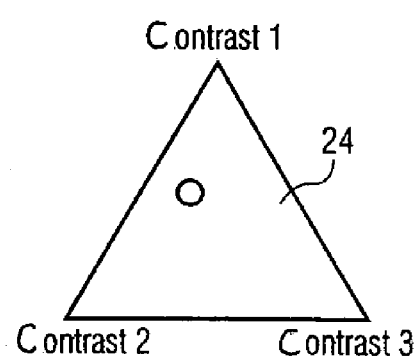
FIG 2b
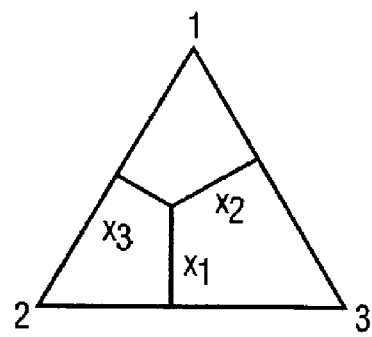
FIG 2c
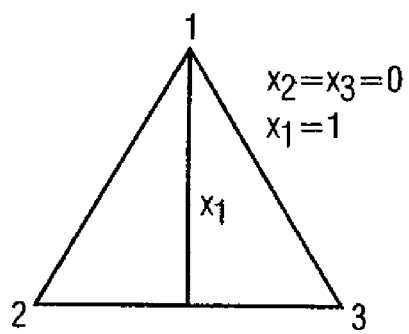
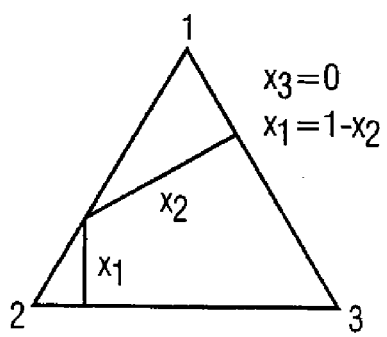

| Element | NMR Frequency in MHz (at 1T) | Relative Detection Sensitivity at the Same Measuring Frequency |
|---|---|---|
| $^1H$ | 42,58 | 100 |
| $^2H$ | 6,53 | 0,006 |
| $^{13}C$ | 10,71 | 0,025 |
| $^{14}N$ | 3,08 | 0,31 |
| $^{17}O$ | 5,77 | 0,049 |
| $^{19}F$ | 40,06 | 0,006 |
| $^{23}Na$ | 11,26 | 0,1 |
| $^{31}P$ | 17,24 | 0,14 |
| $^{35}Cl$ | 4,17 | 0,0084 |
| $^{39}K$ | 1,99 | 0,011 |

MAGNETIC RESONANCE TOMOGRAPHY APPARATUS WITH STEP-FREE FADE BETWEEN DISPLAYED DIFFERENT SPIN ENSEMBLES

BACKGROUND OF THE INVENTION

1. Field of the Invention

The present invention is directed in general to magnetic resonance tomography (MRT) as employed in medicine for examining patients. The present invention is thereby directed to an apparatus for processing and presenting a magnetic resonance tomography measured image as well as to an imaging MR method.

2. Description of the Prior Art

Magnetic resonance tomography is a tomographic method for medical diagnostics that is mainly distinguished by a high contrast resolution capability. Due to the excellent presentation of soft tissue, magnetic resonance tomography has developed into a method that is often superior to x-ray computed tomography. Magnetic resonance tomography is currently based on the application of spin echo sequences and gradient echo sequences that enable an excellent image quality given measuring times on the order of magnitude of minutes.

It is particularly the hydrogen nuclei, that are abundantly present in biological tissue, that enable the production of medically meaningful images. However, heavier magnetic nuclei such as, for example, $^{13}C$, $^{19}F$, $^{23}Na$, $^{31}P$ can also be detected in biological tissue and imaged analogous to the hydrogen nucleus despite their lower concentration. The resonant frequencies of the most important nuclei occurring in biological tissue and their relative detection sensitivity given the same measuring frequency and taking their natural occurrence into consideration are shown by FIG. 3.

In experiments wherein the investigated nuclei are incorporated into different molecules, however, slightly different resonant frequencies are observed given the same magnetic field. This is due to the electrons in the molecule that cause a phenomenon referred to as the "chemical shift". This chemical shift is the property that the resonant frequency is shifted slightly proportionately to the field strength dependent on the type of chemical bond in which the nucleus is situated.

As an example, FIG. 4 shows the phosphorous spectrum of the human thigh muscle at 2T. The metabolites adenosine triphosphate (ATP), creatine phosphate (PCr), in organic phosphate (Pi) and phosphorous diester (PDE) can be distinguished from one another on the basis of their chemical shifts.

Particularly when registering the resonant frequency of hydrogen, artifacts occur at the boundary layers between fat and water in the presentation of the tissue of patients, these artifacts arising from the influence of the chemical shift. Due to their high concentration in the human body, it is mainly hydrogen nuclei of free water and of fat that contribute to the image. Their relative resonant frequency different $\Delta f$ amounts to approximately 3 ppm (parts per million). The $\Delta f$ leads to a relative shift of the images of the two nuclei in the direction of the gradient that is active during the data registration ("read gradient" or "frequency coding gradient"). The extent of the shift is dependent on the bandwidth employed per pixel, which is in turn dependent, among other things, on the field of view and on the matrix size.

In order to facilitate orientation within the anatomy for the user, there is therefore the demand that the signal of one spin type be suppressed either entirely or up to a certain extent.

In general, the fat signal is suppressed because the critical diagnostic information can be obtained from the water signal. Fading in the fat signal (or the incomplete suppression thereof) serves the purpose of anatomical orientation (for example, in orthopedics).

In the registration of the nuclear resonance of hydrogen nuclei, the display of the water image with a permanently set degree of fat suppression is standard. This standard method utilizes the frequency shift between water and fat in order to emit a selective, narrowband RF pulse that only acquires one of the two spin type—preferably fat—and rotates by an angle $\alpha \leq 90°$ in the transverse plane. Due to the application of a suitable gradient pulse (spoiler gradient), the transverse magnetization is completely dephased and only the longitudinal spin portion is still coherent. At $\alpha=90°$, the entire fat part is suppressed since a longitudinal part is no longer present after the application of the RF pulse.

According to the above method, however, the degree of suppression accompanying the presented image was only able to be permanently set by the user before the exposure; variation after the end of the measurement is not possible.

SUMMARY OF THE INVENTION

An object of the present invention is to provide an apparatus for processing and presenting a magnetic resonance tomography measured image with which the presentation of the parts of two or more contrast images can be varied in one measured image after the measurement.

This object is inventively achieved in a device for processing and presenting a magnetic resonance tomography measured image that has a memory for the simultaneous acceptance of at least two contrast images. For example, the contrast images can then have been acquired from different spin ensembles that have respectively different chemical shifts. However, it is also possible for the contrast images to be obtained from different MR images (anatomical, angiographic or functional MR images), i.e. the superimposed image is acquired by fading two or three images of the same anatomy.

This apparatus further has both a picture screen for visualizing the registered contrasts and an input device visualized on the picture screen for selecting the contrasts.

Inventively, the input device enables a step-free fading between two or three registered contrast images.

The input device for two contrast images can be realized in the form of a linear slide and that for three contrast images can be realized in the form of a triangular controller.

Particularly given contrast images on the basis of spin ensembles, the first spin ensemble can be water and the second spin ensemble can be fat.

The simultaneous registration of the contrasts ensues in the processing device either by means of the Dixon method or by suppressing the signal of the other spin ensemble according to the standard method.

The contrast presentation of the respective spin ensembles can ensue with different colors.

DESCRIPTION OF THE DRAWINGS

FIG. 2a shows an input device for a 2-contrast fade in the form of a one-dimensional slide.

FIG. 2b shows an input device for a 3-contrast fade in the form of a triangular controller.

FIG. 2c shows possible settings of the triangular controller.

DESCRIPTION OF THE PREFERRED EMBODIMENTS

Figure 1:
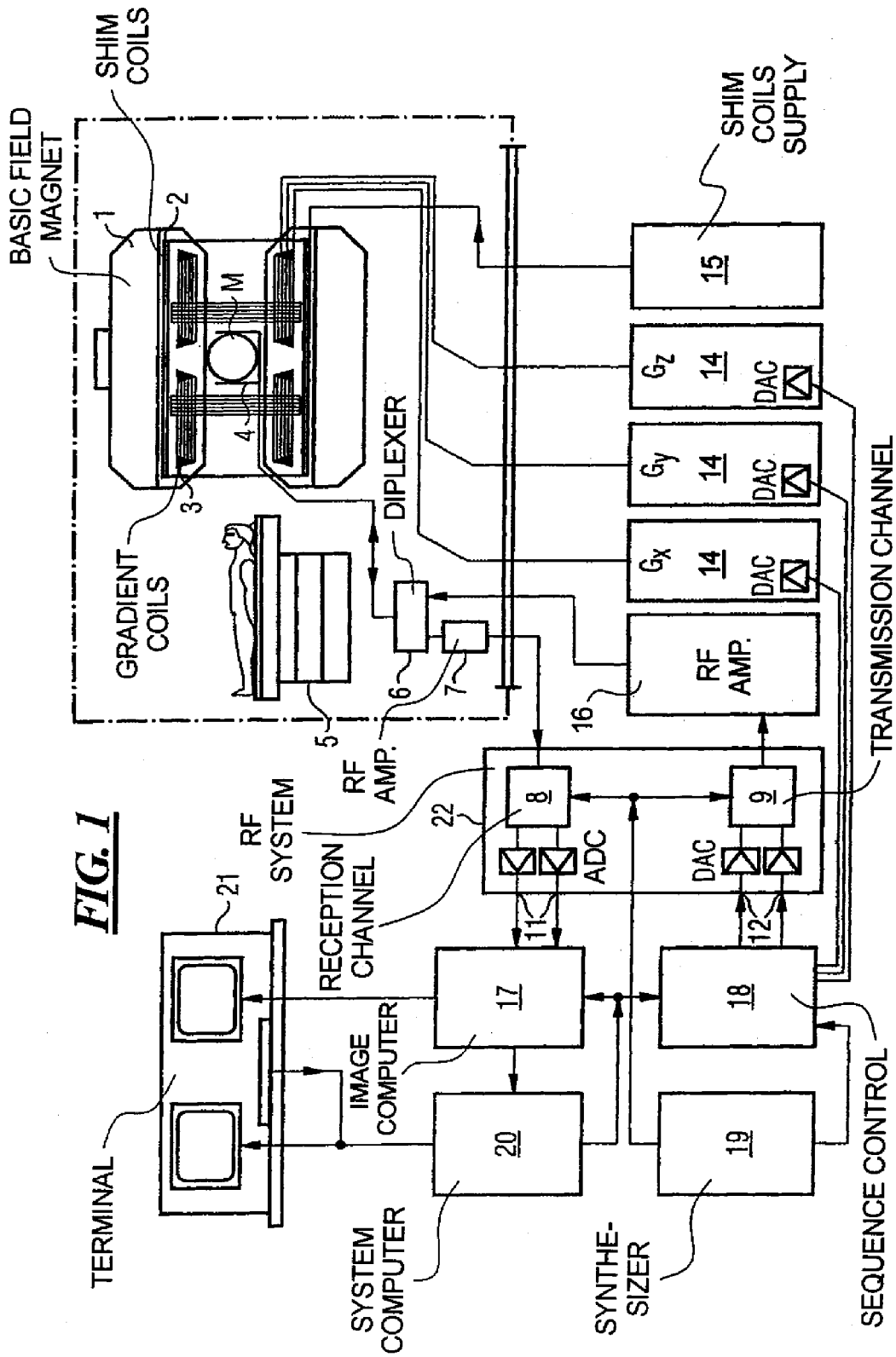
FIG. 1 schematically shows a magnetic resonance tomography apparatus constructed and operated according to the invention.
Figures 3, 4:
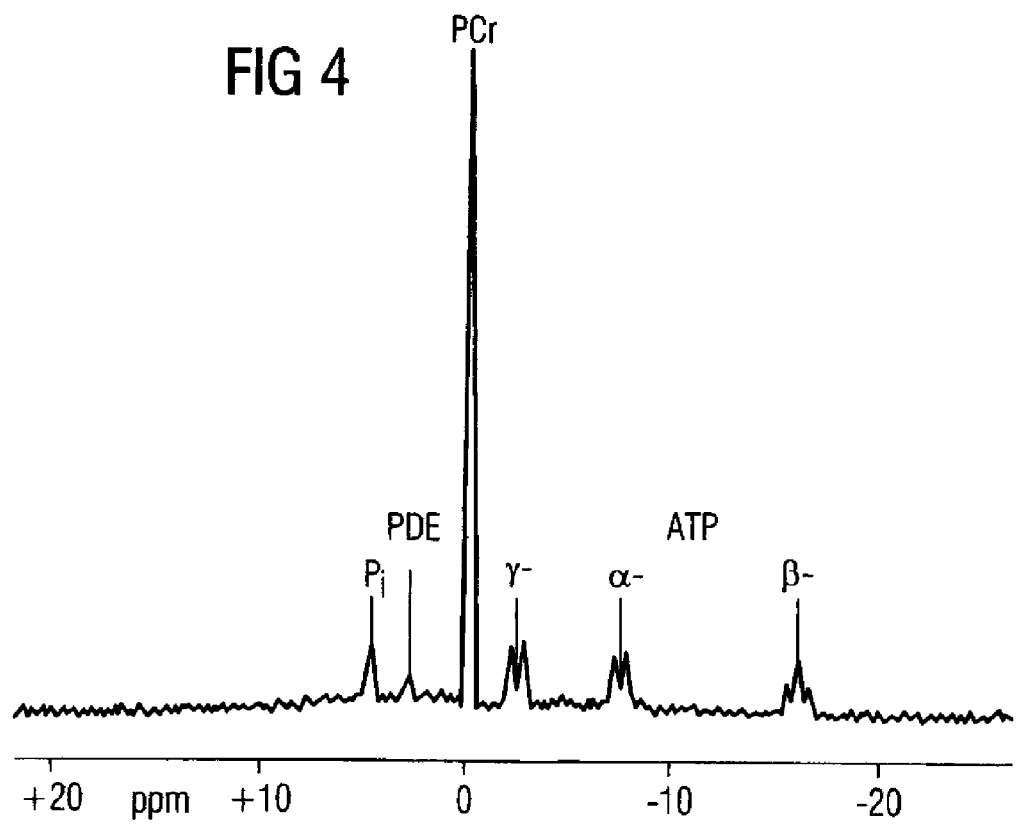
FIG. 3, as noted above, shows the resonant frequencies of the most important nuclei occurring in biological tissue and their relative detection sensitivity.
FIG. 4, as noted above, shows the phosphorous spectrum of the human thigh muscle at 2T.

FIG. 1 is a schematic illustration of a magnetic resonance tomography apparatus for generating a magnetic resonance image of a subject according to the present invention. The structure of the nuclear magnetic resonance tomography apparatus corresponds to the structure of a conventional tomography apparatus, with the differences noted below. A basic field magnet 1 generates a time-constant, strong magnetic field for polarization or alignment of the nuclear spins in the examination region of a subject such as, for example, a part of a human body to be examined. The high homogeneity of the basic magnetic field required for magnetic resonance measurement is present in a spherical measurement volume M into which the parts of the human body to be examined are introduced. For supporting the homogeneity demands and, in particular, for eliminating time-invariable influences, shim plates of ferromagnetic material are attached at suitable locations. Time-variable influences are eliminated by shim coils 2 that are driven by a shim power supply 15.

A gradient coil system 3 that is composed of three partial windings is utilized in the basic field magnet 1. Respective amplifiers 14 supply the partial windings with current for generating a linear gradient fields in the respected directions of the Cartesian coordinate system. The first partial winding of the gradient field system 3 thereby generates a gradient $G_x$ in the x-direction, the second partial winding generates a gradient $G_y$ in the y-direction, and the third partial winding generates a gradient $G_z$ in the z-direction. Each amplifier 14 has a digital-to-analog converter that is driven by a sequence control 18 for generating gradient pulses at the proper time.

A radio-frequency antenna 4 is situated within the gradient field system 3, and converts the radio-frequency pulses emitted by a radio-frequency power amplifier 30 into an alternating magnetic field for exciting the nuclei and for aligning the nuclear spins of the subject under examination, or of a region of the subject under examination. The radio frequency antenna 4 also converts the alternating field emanating from the precessing nuclear spins, i.e. the magnetic resonance echo signals produced as a rule by a pulse sequence composed of one or more radio-frequency pulses and one or more gradient pulses, into a voltage that is supplied via an amplifier 7 to a radio frequency reception channel 8 of a radio-frequency system 22. The radio-frequency system 22 also has a transmission channel 9 wherein the radio-frequency pulses for exciting the magnetic nuclear resonance are generated. The respective radio frequency pulses are digitally presented as a sequence of complex numbers on the basis of a pulse sequence in the sequence control 18 prescribed by the system computer 20. As a real part and an imaginary part, this number sequence is supplied via respective inputs 12 to a digital-to-analog converter in the radio frequency system 22 and is supplied from the latter to a transmission channel 9. In the transmission channel 9, the pulse sequences are modulated onto a radio-frequency carrier signal whose basic frequency corresponds to the resonant frequency of the nuclear spins in the measurement volume.

The switching from transmission mode to reception mode ensues via a transmission/reception duplexer 6. The radio-frequency antenna 4 emits the radio-frequency pulses for exciting the nuclear spins into the measurement volume M and samples resulting echo signals. The correspondingly acquired magnetic resonance signals are demodulated in phase-sensitive fashion in the reception channel 8 of the radio frequency system 22 and are converted via the respective analog-to-digital converter into a real part and an imaginary part of the measured signal. An image is reconstructed from the measured data acquired in this way by an image computer 17. The administration of the measured data, the image data and the control programs ensues via the system computer 20. On the basis of a prescription with control programs, the sequence control 18 controls the generation of the desired pulse sequences and the corresponding sampling of k-space. In particular, the sequence control 18 controls the switching of the gradients at the correct time, the transmission of the radio frequency pulses with defined phase and amplitude, as well as the reception of the magnetic resonance signals. The time base for the radio-frequency system 22 and the sequence control 18 is made available by a synthesizer 19. The selection of corresponding control programs for generating a nuclear magnetic resonance image as well as the presentation of the generated nuclear magnetic resonant image ensues via a console 21 that has a keyboard as well as one or more picture screens.

The basic idea of the present invention is to separately generate the nuclear magnetic resonance tomography images of two or three contrast images. This ensues by separate exposures according to the above method or by means of the two-point or multi-point method of Dixon.

When the image information, i.e. the contrast images of the spin types or ensembles, for example given two types such as fat and water, are present separately in a memory 25 of the image computer 17, the software of the system computer 20 is capable of linearly generating a step-free fade pixel-by-pixel from a pure water image to a pure fat image within a presentation region:

$$\mathrm{Sum}(x) = \mathrm{Fat}^*(1-x) + \mathrm{Water}^* x$$

A pure fat image is obtained for x=0; a pure water image is obtained for x=1; an equal weighting is obtained for x=0.5. (Fat and water are only as examples here.) A control of the parameter x ensues via an input interface at the terminal 21 as shown by way of example in FIG. 2a. A one-dimensional slide 23 (FIG. 2a) suffices for a 2-contrast fade. This slide exhibits 100% contrast 1 at the left end and 100% contrast 2 at the right end as well as 50-50 contrast in the middle position and correspondingly continuous transitions.

When the simultaneous acceptance of three spin types is present in the memory 25, a triangular controller 24 (FIG. 2b) can be employed for 3-contrast fading. The position in one of the three corners is interpreted as 100% of the appertaining contrast and the middle position is interpreted as ⅓-⅓-⅓ of the three contrasts; positions at a triangular boundary between two contrasts fade between two of the three contrasts.

FIG. 2c shows how the 3-contrast control is computationally converted: the length of the perpendicular onto the opposite side of the triangle represents the degree of the respective contrast part.

The overall length of the parts is thereby normed:

$$x_1 + x_2 + x_3 = 1$$

The 3-contrast image derives from the weighting of the perpendiculars with the corresponding contrast parts:

$$x_1^* \mathrm{Contrast1} + x_2^* \mathrm{Contrast2} + x_3^* \mathrm{Contrast3}$$

One command (for example one of the mouse keys or the keyboard) suffices for activating the contrast control and, subsequently, the motion of the input device in one dimension (for the 2-contrast control) or in two dimensions (for the 3-contrast control). This input device can be but need not be the mouse. The motion is converted onto the position of the position/contrast indicator with an arbitrarily constituted "translation".

Ideally, a dynamic fade can thus be made from, for example, a pure water presentation onto a pure fat presentation or onto the presentation of a third type. A multi-color presentation (for example blue levels for water, red levels for fat, etc.) would be conceivable in addition to the normal gray scale presentation.

It must be noted that the above explanations apply identically where the contrast images are composed of a MR images of different types, for example anatomical, angiographic or functional MR images.

Although modifications and changes may be suggested by those skilled in the art, it is in the intention of the inventors to embody within the patent warranted hereon all changes and modifications as reasonably and properly come within the scope of their contribution to the art.

We claim as our invention:

1. An apparatus for processing and presenting a magnetic resonance tomograph image, comprising:
    a computer having a memory in which at least three images, each obtained by a magnetic resonance measurement, are stored, as stored images;
    a display screen connected to said computer for visually displaying one magnetic resonance tomography image as a superimposition of three of said stored images, as a displayed image;
    said computer being configured to cause an input device to be visually represented on said display screen for selecting a contrast of said displayed image at a contrast value dependent on the respective three of said stored images, said computer visually representing said input device as a triangle having apexes respectively representing the contrasts of said three of said stored images each apex representing 100% of the contrast of the stored image represented by that apex, and a cursor moveable within said triangle; and
    said computer including a processor that is configured to calculate said displayed image from said three of said stored images dependent on the contrast selected with said input device by movement of said cursor within said triangle to vary a degree of superimposition of at least portions of said three of said stored images in said displayed image at said display screen dependent on respective distances of said cursor from said apexes, after said magnetic resonance measurement.

2. An apparatus as claimed in claim 1 wherein actuation of said input device allows a step-free selection of said degree of superimposition, and thus of said value for said contrast of said displayed image, of said three of said stored images.

3. An apparatus as claimed in claim 1 wherein said at least three stored images are respectively different types of magnetic resonance images.

4. An apparatus as claimed in claim 3 wherein said at least three stored images are respectively obtained from difference spin ensembles having different chemical shifts.

5. An apparatus as claimed in claim 4 wherein one of said at least three stored images represents a water spin ensemble and wherein another of said stored images represents a fat ensemble.

6. An apparatus as claimed in claim 1 wherein said processor simultaneously calculates said at least three stored images using the Dixon method.

7. An apparatus as claimed in claim 1 wherein said at least three stored images are respectively based on different magnetic resonance spins ensembles having respectively different chemical shifts, and wherein said processor calculates said at least three stored images by suppressing signals from a selected spin ensemble in each of said stored images.

8. An apparatus as claimed in claim 1 wherein said computer visually represents the respectively different contrasts of said three of said stored images by different colors.

* * * * *